US011026893B2

(12) United States Patent
Berkland et al.

(10) Patent No.: US 11,026,893 B2
(45) Date of Patent: Jun. 8, 2021

(54) TASTE MASKING DRUG FORMULATIONS

(71) Applicant: ADARE PHARMACEUTICALS USA, INC., Lawrenceville, NJ (US)

(72) Inventors: Cory Berkland, Lawrence, KS (US); Milind Singh, Apex, NC (US)

(73) Assignee: Adare Pharmaceuticals USA, Inc., Lawrenceville, NJ (US)

( * ) Notice: Subject to any disclaimer, the term of this patent is extended or adjusted under 35 U.S.C. 154(b) by 0 days.

(21) Appl. No.: 16/542,986

(22) Filed: Aug. 16, 2019

(65) Prior Publication Data

US 2019/0365655 A1 Dec. 5, 2019

Related U.S. Application Data

(60) Division of application No. 15/244,455, filed on Aug. 23, 2016, now Pat. No. 10,426,734, which is a continuation of application No. PCT/US2015/017485, filed on Feb. 25, 2015.

(60) Provisional application No. 61/944,152, filed on Feb. 25, 2014.

(51) Int. Cl.
| | | |
|---|---|---|
| *A61K 9/50* | (2006.01) | |
| *A61K 9/00* | (2006.01) | |
| *A61K 31/426* | (2006.01) | |
| *A61K 31/573* | (2006.01) | |
| *A61K 47/10* | (2017.01) | |

(52) U.S. Cl.
CPC .......... *A61K 9/5026* (2013.01); *A61K 9/0053* (2013.01); *A61K 9/5015* (2013.01); *A61K 9/5063* (2013.01); *A61K 9/5089* (2013.01); *A61K 31/426* (2013.01); *A61K 31/573* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 4,800,087 A | 1/1989 | Mehta | |
| 5,084,278 A | 1/1992 | Mehta | |
| 5,578,316 A | 11/1996 | Bhardwaj et al. | |
| 5,614,222 A | 3/1997 | Kaplan | |
| 6,221,402 B1 | 4/2001 | Itoh et al. | |
| 6,660,382 B2 | 12/2003 | Nouri et al. | |
| 6,669,961 B2 | 12/2003 | Kim et al. | |
| 10,426,734 B2 | 10/2019 | Berkland et al. | |
| 2003/0157326 A1 | 8/2003 | Vaghefi et al. | |
| 2004/0121003 A1 | 6/2004 | Chickering et al. | |
| 2004/0258752 A1 | 12/2004 | Paruthi et al. | |
| 2005/0136114 A1 | 6/2005 | Kulkarni et al. | |
| 2005/0269722 A1 | 12/2005 | De Luigi Brushei et al. | |
| 2006/0078614 A1 | 4/2006 | Venkatesh | |
| 2006/0141053 A1 | 6/2006 | Menjoge et al. | |
| 2007/0098796 A1 | 5/2007 | Rekhi et al. | |
| 2008/0020018 A1 | 1/2008 | Moodley et al. | |
| 2010/0173002 A1 | 7/2010 | Yulai et al. | |
| 2011/0250281 A1 | 10/2011 | Mapelli et al. | |
| 2013/0149383 A1 | 6/2013 | Berkland et al. | |

FOREIGN PATENT DOCUMENTS

| | | |
|---|---|---|
| EP | 0409254 | 1/1991 |
| WO | 200152848 | 7/2001 |
| WO | WO2008056344 A2 * | 5/2008 |
| WO | 2009078034 | 6/2009 |
| WO | 2013024023 | 2/2013 |
| WO | 2013090452 | 6/2013 |
| WO | WO 2015/130760 A1 | 9/2015 |

OTHER PUBLICATIONS

Law, et al. "Ritonavir-PEG 8000 Amorphous Solid Dispersions: In Vitro and In Vivo Evaluations." Journal of Pharmaceutical Sciences, vol. 93, No. 3, Mar. 2004.
Law, et al. "Physicochemical Considerations in the Preparation of Amorphous Ritonavir-Poly(ethylene glycol) 8000 Solid Dispersions." Journal of Pharmaceutical Sciences, vol. 90, No. 8, Aug. 2001.
Innovations in Pharmaceutical Technology, "Masking the taste of fast-disintegrating tablets", vol. 14, No. 4, Jan. 1, 2004 (Jan. 1, 2004), pp. 109-111.
European Search Report dated Jul. 11, 2017 for European Patent Application No. 14852021.6.
U.S. Appl. No. 15/244,455, filed Aug. 23, 2016, US 2016-0354317 A1, Dec. 8, 2016, U.S. Pat. No. 10,426,734, Oct. 1, 2019, Registered.
International Preliminary Report on Patentability in International Application No. PCT/US2015/017485, dated Aug. 30, 2016, 10 pages.
International Search Report and Written Opinion in International Application No. PCT/US2015/017485, dated Jul. 2, 2015, 13 pages.
Invitation to Pay Additional Fees in International Application No. PCT/US2015/017485, dated Apr. 22, 2015, 2 pages.

* cited by examiner

*Primary Examiner* — Robert A Wax
*Assistant Examiner* — Randeep Singh
(74) *Attorney, Agent, or Firm* — Cooley LLP

(57) ABSTRACT

The present disclosure relates to a taste-masking microcapsule composition. The composition comprises a core portion encapsulated by a shell portion. The core portion comprises an active pharmaceutical ingredient (API) and one or more excipients. The shell portion comprises a hydrophobic matrix and a pH-responsive material. The microcapsule compositions prevent API release at the more neutral pH levels in the oral cavity, but upon exposure to pH levels of the stomach, the pH-responsive material becomes soluble thereby permitting release of the API.

15 Claims, 5 Drawing Sheets

TASTE MASKING DRUG FORMULATIONS

CROSS-REFERENCE TO RELATED APPLICATIONS

The present application is a divisional of U.S. patent application Ser. No. 15/244,455, filed on Aug. 23, 2016, which is a continuation of PCT/US2015/017485, filed on Feb. 25, 2015, which claims priority to U.S. Provisional Application No. 61/944,152 filed on Feb. 25, 2014, each of which is incorporated herein by reference in its entirety.

BACKGROUND

Upwards of 79% of children discharged from pediatric hospitals are prescribed one or more medications that are designed, approved, and intended for use in adults, underscoring the need for pediatric-specific formulations. In the absence of pediatric-specific dosages, formulations that are both palatable (to ensure compliance) and titratable (to meet the weight/surface area-appropriate dosage needs from neonates to adolescents), health-care providers either: (i) prescribe adult-approved liquid formulations; or (ii) manipulate available products to create extemporaneous formulations (e.g., by crushing a tablet). Liquid suspensions, while titratable and largely preferred by children over tablets and capsules, are often poorly palatable (i.e. liquid forms of prednisone and ritonavir) resulting in poor compliance. Extemporaneous formulations can alter the performance including the palatability and bioavailability of the original product thereby contributing to both poor compliance (only 70% compliance in hospitals) and increased risk for under and over-dosing. Free flowing drug-loaded microcapsule powders would allow pharmacists to prepare highly palatable microcapsule liquid suspensions to accurately dose children of all ages.

SUMMARY

The present compositions and methods are based on the discovery that release profiles, bioavailability, and palatability can be precisely controlled by a microcapsule formulation comprising a drug-rich core encapsulated in a pH-responsive shell. The pH-responsive shell being insoluble at pH levels associated with the oral cavity, but soluble at pH levels associated with stomach or other region of the gastrointestinal system thereby preventing release of the active pharmaceutical ingredient until the appropriate pH is encountered. The drug rich core of the microcapsule may be formulated with appropriate excipients to permit the desired release profile, whether immediate or extended-release. Methods of producing these compositions is also provided.

Thus, in one embodiment, the present composition comprises a microcapsule having a core portion encapsulated by a shell portion. The core portion comprising an active pharmaceutical ingredient and an excipient. The shell portion comprising a hydrophobic matrix and a pH-responsive material.

The active pharmaceutical ingredient may comprise any agent that is used as a therapeutic and more particularly, a therapeutic that presents a foul taste. Examples of particular active pharmaceutical ingredients discussed herein include prednisone and ritonavir.

The excipient that is used with the active pharmaceutical ingredient may, in some instances, be dependent on the properties of the active ingredient. For example, a hydrophilic excipient may be used in connection with a hydrophobic active ingredient. Furthermore, the excipient may be chosen to provide particular release profiles. Examples of suitable classes of excipients include, but are not limited to waxes, lipids, polyethylene glycol (e.g. PEG 2000 and PEG 6000), polyols, stearates, and block copolymers. In particular embodiments, when the active pharmaceutical ingredient is prednisone or ritonavir, polyethylene glycol is a suitable excipient.

The shell portion comprises a hydrophobic matrix and a pH-responsive material. In one particular example, the pH-responsive material is insoluble at a pH of greater than 5.0 or are otherwise insoluble in saliva, but that are soluble at a pH of less than 5.0. In other embodiments, the pH-responsive material may be soluble or insoluble at various other pH levels encountered in the gastrointestinal system based on the desired release profile. Examples of pH-responsive materials include butylated methacrylate copolymer (Eudragit® E-100 PO), amino methacrylate copolymer, aminoakyl methacrylate copolymer, hydroxypropylmethycellulose phthalate, hypromellose phthalate, polyacrylates derivatives, and polymethacrylates derivatives.

The hydrophobic matrix component of the shell may include one or more of glycerol fatty acid esters, high molecular weight glycols (e.g., polyethylene glycol with a minimum of 20 repeating units), cellulose ethers (e.g., ethyl cellulose, hydroxypropyl cellulose, hydroxypropyl methyl cellulose, microcrystalline cellulose), cellulose esters (e.g., cellulose acetate, cellulose acetate phthalate, hydroxypropyl methyl cellulose phthalate), poloxamers, starch, stearic acid, ceresine wax, beeswax, ozokerite, microcrystalline wax, candelilla wax, montan wax, carnauba wax, paraffin wax, cauassu wax, Japan wax, and Shellac wax.

The composition of any of the above embodiments may comprise a plurality of microcapsules having a mean particle diameter from about 50 µm to about 500 µm, from about 100 µm to about 400 µm, from about 150 µm to about 300 µm, and generally about 200 µm, wherein at least about 80% of the microcapsules have a particle diameter within 1-25%, 2-20%, 5-15%, and generally within 10% of the mean particle diameter.

The composition of any of the above embodiments may be provided in a variety of formats including liquid suspensions, chewable tablets, and effervescent tablets.

A method of producing the various microcapsule compositions is also provided. In one embodiment, the method comprises the following steps: (1) dissolving an active pharmaceutical ingredient in ethanol to produce an active pharmaceutical ingredient-ethanol mixture; (2) co-melting the active pharmaceutical ingredient ~ethanol mixture with a molten excipient to provide a core dispersion; (3) melting a polymer and a lipid to form a shell mixture; and (4) applying the core dispersion through a central portion of a nozzle and simultaneously applying the shell mixture through an annular portion of the nozzle surrounding the central portion in the presence of vibrational excitation thereby forming the microcapsule, wherein the microcapsule comprises a core portion and a shell portion. The method may further comprise the step of applying a stabilizing air stream to the nozzle as the microcapsule exits the nozzle to reduce the diameter of the microcapsule. The method may be performed with any combination of active pharmaceutical ingredient, excipient, polymer, and hydrophobic matrix combination described herein for the various microcapsule compositions.

BRIEF DESCRIPTION OF THE DRAWINGS

In addition to the drawings described below, additional drawings are provided summarized in the presentation set out in Appendix A, attached hereto.

DESCRIPTION

Figure 1:
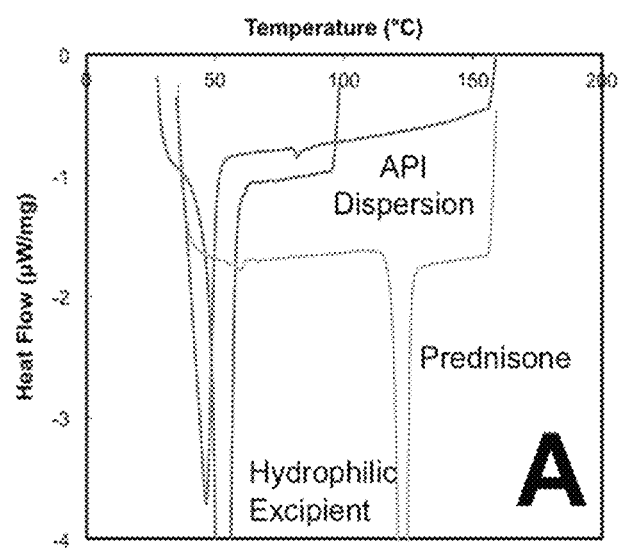
FIG. 1 provides DSC thermograms of APIs and their dispersions in hydrophilic matrix. Both prednisone (A) and ritonavir (B) demonstrate that they are dispersed within the matrix in an amorphous manner, due to lack of discrete drug melting peaks. A low crystallization of drug will also expedite dissolution once the microcapsule shell has degraded.
Figure 1:
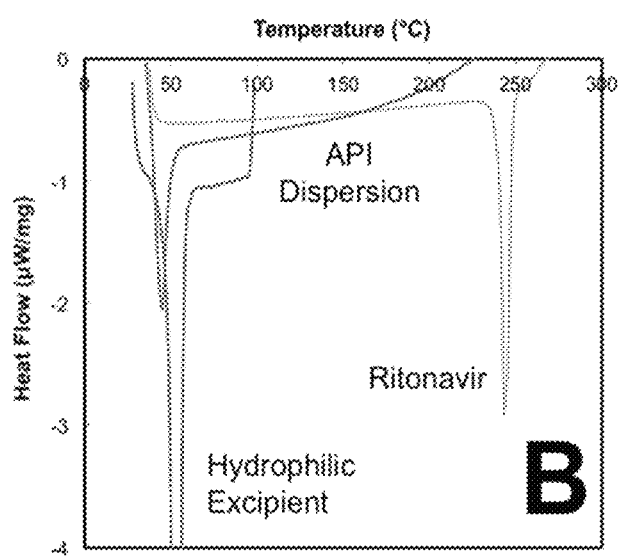

The present disclosure generally relates to taste masking formulations of compounds that permit accurate dosing and the ability to process into a variety of dosing formats as well as processes for manufacturing the same.

It is often difficult for formulation scientists to develop a dosage that offers both a high level of taste-masking as well as immediate and complete release soon after the dosage form clears the oral cavity. This is especially true for the foulest-tasting drugs given that most taste-masking techniques rely on adding progressively thicker taste-masking shells to progressively reduce drug release through the shell in the oral cavity. Unfortunately, after passing through the oral cavity, this same taste-masking shell coating is a barrier to rapid release.

To address this problem, the present disclosure describes, in one embodiment, a pH-responsive shell that is insoluble at the neutral pHs found in the oral cavity, but readily dissolves at the acidic pHs found in the stomach, thereby limiting the release of the drug-loaded core until it reaches the stomach.

More generally, the present disclosure provides a composition that comprises a plurality of microcapsules with each microcapsule comprising a core portion and a shell portion. The core portion comprises an active pharmaceutical ingredient (API) and an excipient. The shell portion comprises a pH-responsive material and a hydrophobic matrix component.

The core portion is designed to maximize API loading and to permit formulation of the API that provides a rapid dissolution upon exposure to an aqueous environment. In order to meet these goals, the core portion should include a balance between API and excipient that will provide a finely dispersed (solid dispersion) or dissolved (solid solution) state prior to particle hardening. The excipients utilized in the core portion are at least in part dependent on the properties of the API, for example, the API's hydrophilicity or hydrophobicity. Thus, in certain embodiments, the excipients are hydrophilic. Furthermore, the excipients, in order to maximize API loading, may promote homogenous dispersion, solubilization or the ability to complex with the API. For example, the excipients are selected from the group consisting of waxes, lipids, polyethylene glycol (PEG), polyols, stearates, and block copolymers including poloxamers and lutrols.

The API may include a variety of compounds including, but not limited to those that are foul-tasting and generally not readily available in a formulation that allows for consistent and safe dosing formats in pediatric patients. In one specific example, the API is selected from the group consisting of prednisone and ritonavir. The percentage of API in the core can be from about 1% to 100% (100% in the instance the API itself is in the form of a liquid such as melted drug or vitamin E). Additionally, the percentage of API in the core portion can be from about 1% to 50%, from about 1% to 25%, and from about 1% to about 10%. In the instance the API cannot be melted or dissolved (i.e. fine drug particles in suspension), the percentage of API in the core portion can be equal to or less than 10%. For any of the above percentages of API, the balance of the core portion may be one or more excipients.

The shell portion is designed to promote stability by protecting the core formulation from the storage environment and to regulate core release during administration to a patient. The storage environment may be aqueous, an oil-suspending agent, or simply air with a standard humidity content. In order to regulate release, the shell portion may comprise materials that are responsive to specific pH ranges, temperature changes, and other unique physiochemical properties including degree of hydration or response to specific enzymes.

For the stabilizing or hydrophobic matrix component of the shell portion, suitable materials include those that are not approaching any phase transitions at room temperatures such as waxes, lipids, and high molecular weight copolymers. Examples of suitable hydrophobic matrix materials include carnauba wax, glyceril tristearate, glyceril trimyristate, beeswax, candellila wax, stearyl alcohol, stearic acid, gylceryl monostearate, ethyl cellulose, hydroxpropylmethylcellulose, poly(ethylene glycol), sorbitan oleate, sorbitan monooleate, poloxamers, and gelatin, and various combinations thereof.

For the pH-responsive material, also referred to as the "release-responsive component," suitable materials include those that are soluble at pH levels encountered in the stomach (<5.0), but insoluble at pH levels encountered in the oral cavity (>5.0) or otherwise insoluble in saliva. Examples of such pH-responsive materials include methacrylate copolymer, butylated methacrylate copolymer, basic butylated methacrylate copolymer (Eudragit® E) or poly(methacrylic acid), and may alternatively include hydration-responsive polymer networks such as hydrogels. The responsive release component may comprise a percentage of shell portion that is based on the degree of protection the API requires, its potential range of action, and the intended trigger conditions. The release responsive component can comprise from about 1% to about 100% of the shell portion (100% where the release responsive component can also act as a stabilizing component). Additionally, the percentage of release responsive component in the shell portion can be from about 1% to 50%, from about 1% to 25%, and from about 1% to about 10%. In some instances, the release responsive component can be used in a very small fraction where its action is dramatic enough to affect the morphology of the core/shell particle. For any of the above percentages of release responsive component, the balance of the shell portion may comprise one or more hydrophobic matrix components.

In any of the embodiments described herein, the microcapsules of the composition may comprise a particle diameter of from about 50 μm to about 500 μm, from about 100 μm to about 400 μm, from about 150 μm to about 350 μm, or from about 200 μm to about 300 μm. In another embodiment, the microcapsules of the composition may comprise a mean particle diameter of from about 50 μm to about 500 μm, from about 100 μm to about 400 μm, from about 150 μm to about 350 μm, or from about 200 μm to about 300 μm.

For any of the embodiments described herein, relatively tight particle size distributions may be preferred. Such particle size distributions benefit from the lack of "fines." Particle fines are small particles left over from a manufacturing process. Their small effective surface area results in faster dissolution rates. As used herein, the term "fines" refers to particulates having a particle size at or below 10% of the mean particle size diameter. Accordingly, formulations having particle fines are not substantially monodisperse and may not provide the desired dissolution properties and/or bioavailability. Thus, at least 80%, and in some instances at least 90%, and in other instances about 100% of the microcapsules in a composition have a particle diameter that deviates from the mean particle diameter by about 25% to about 1%, by about 20% to about 2%, by about 15% to about 5%, and generally 10% or less, thus allowing for precise control of release properties.

The embodiments of the present composition described herein may provide for extended release and/or immediate release profiles. In one embodiment, the present composition is capable of mitigating release of the API during the first two minutes in an oral environment and upon encountering an acidic environment, such as in the stomach and gastrointestinal tract, providing an accelerated release with full dissolution of the API at 30 minutes.

In one particular embodiment, the present composition comprises a plurality of microcapsules, each microcapsule having a core component comprising about from about 2.5% to about 15% of prednisone and about 85% to about 97.5% of PEG 2000 or 6000, and a shell component comprising about 10-20% Eudragit® E PO, about 80-90% stearic acid, and optionally about 10% beeswax. Alternatively, in this embodiment, the shell component may comprise about 50-70% carnauba wax, 10-20% beeswax, 5-10% stearic acid, and 5-10% Eudragit® E PO.

In another particular embodiment, the present composition comprises a plurality of microcapsules having a core component comprising about 2.5-20% ritonavir and about 80-97.5% PEG 2000 or 6000 and a shell component comprising about 10-20% Eudragit® E PO, about 80% stearic acid, and optionally about 10% beeswax.

The composition of any of the above embodiments may be provided in a variety of formats including liquid suspensions, chewable tablets, and effervescent tablets.

The present disclosure further provides methods for producing the compositions described herein. In one embodiment, the method comprises the following steps: (1) dissolving the API in ethanol; (2) co-melting the API-ethanol mixture with molten excipient to provide a core portion; (3) co-melting a stabilizing component with a release responsive component to form a shell portion; (4) forming microcapsules from the core portion and shell portion using precision particle fabrication. The precision particle fabrication (PPF) is described in more detail in U.S. Pat. No. 6,669,961, which is incorporated herein by reference in its entirety. Briefly, in PPF, a core portion solution is sprayed through a nozzle with (i) vibrational excitation to produce uniform droplets, (ii) an annular shell solution which blankets the core component, and (iii) a stabilizing air stream to reduce the diameter of the exiting jet.

EXAMPLES

In the following Examples, ORB-101 refers to an exemplary composition of the present disclosure wherein the API is prednisone and ORB-102 refers to an exemplary composition of the present disclosure wherein the API is ritonavir.
Poorly Water-Soluble APIs can be Microencapsulated at High Drug Loadings by Utilizing Solid Dispersion Techniques Traditional delivery approaches for prednisone and ritonavir either involve tableting or syrup/suspension formulations, as these allow high drug loading and immediate bioavailability. The major drawback associated with these formulations is palatability. Both prednisone and ritonavir are exceptionally foul-tasting, which makes oral administration unpleasant or even unattainable in pediatric populations, as even a small fraction of drug on the surface of a tablet, or dispersed freely in a syrup, is detectable by the gustatory system. Moreover, there is an increasing demand for novel formulations that can completely taste-mask drugs such as prednisone and ritonavir without sacrificing immediate bioavailability.

To this end, a pre-formulation solid dispersion of the API in 100% ethanol was created and then added to a hydrophilic excipient in molten form, which addressed the processibility and dissolution aspects, respectively. When heated for prolonged periods, ethanol was vaporized, leaving a uniform suspension of the API in melted excipient. Differential Scanning calorimetry (DSC) thermograms generated on the raw materials and formulations demonstrated that the dispersion process was effective in creating amorphous distribution of drug in the solutions (FIG. 1). Moreover, these solutions were then ready to process via PPF as the cores for ORB-101 and ORB-102.
Drug-Free Shells can be Made from Lipids and/or pH-Responsive Materials Using a Single Step with PPF.

Figure 2:
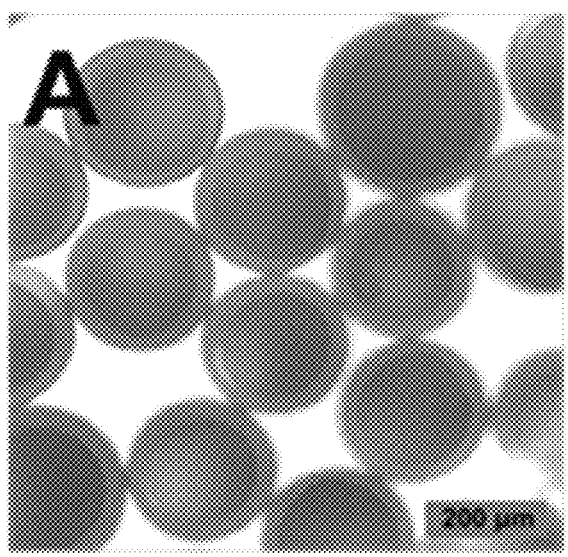
FIG. 2 provides light microscopy images of prednisone (A) and ritonavir (B) microcapsules according to the present disclosure. A distinct core and shell can be seen in both types of powders.
Figure 2:
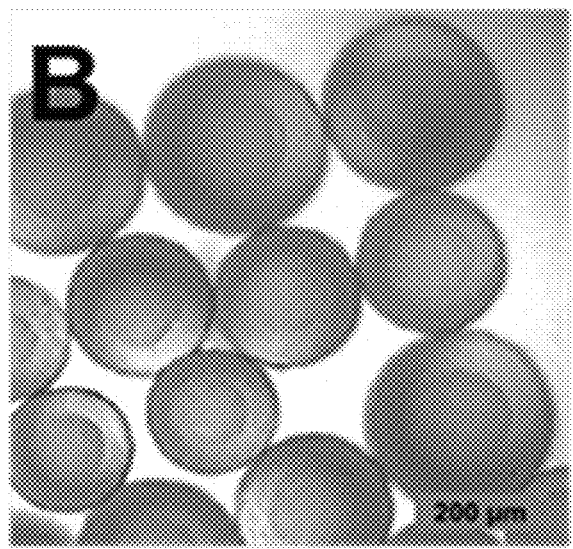

Once formulation development on the "core" solutions was complete, "shell" materials for microscopic capsule formation were investigated. Three commonly used oral excipients were investigated: two lipids and a pH-responsive ionic copolymer. The main goal of this Example was to determine which shell materials could provide a protective coating for the ORB-101 and ORB-102 cores, and yield a fine, dry, flowable powder after the water-free microencapsulation process. Specifically, different combinations of the drug-free excipients were melted and co-flowed around the drug-rich core solutions in a custom PPF nozzle, which yielded microcapsules between 200 and 300 μm (FIG. 2). Typical capsule formulations with a mean particle diameter of 200 μm attained drug loadings of prednisone and ritonavir at 4.8±0.3% w/w and 6.5±0.2% w/w, respectively.
Core-Shell ORB-101 and ORB-102 Capsules Exhibit Delayed and Accelerated Release Kinetics in Neutral and Acidic Environments, Respectively.

The ORB-101 and ORB-102 formulations were iteratively tested for dissolution properties in a United States Pharmacopeia (USP) Type II apparatus at 37° C. in both neutral and acidic environments. Particular attention was paid to the release kinetics of the formulation during the first 2 minutes, as this is the most critical period for indicating taste-masking ability in vitro. The prednisone and ritonavir microcapsules ORB-101 and ORB-102 were also compared to commercially available liquid formulations of the drugs, prednisone and Norvir, respectively.

Figure 3:
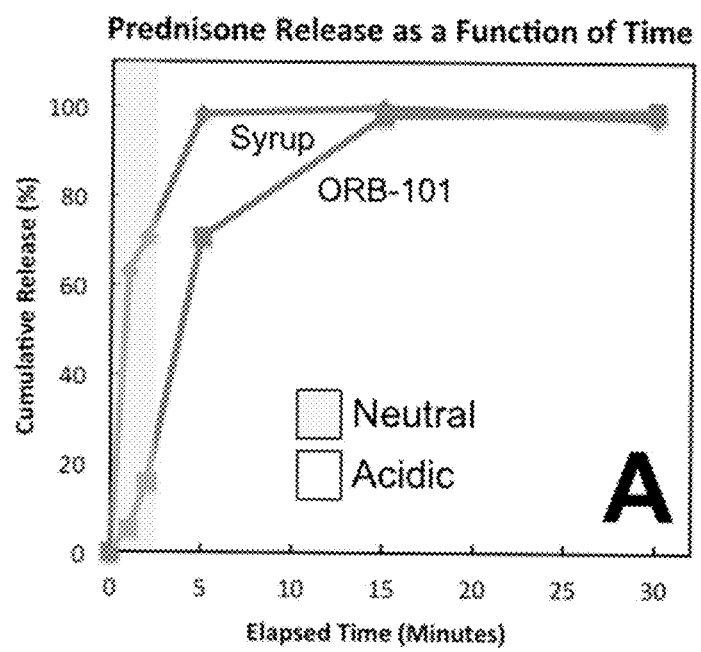
FIG. 3 provides dissolution profiles of prednisone (A) and ritonavir (B) microcapsules of the present disclosure in neutral and acidic conditions, compared to their RLD syrup formulations. In the first 2 minutes (yellow), the microcapsule formulations mitigate drug release in a neutral environment, then quickly release the API thereafter.
Figure 3:
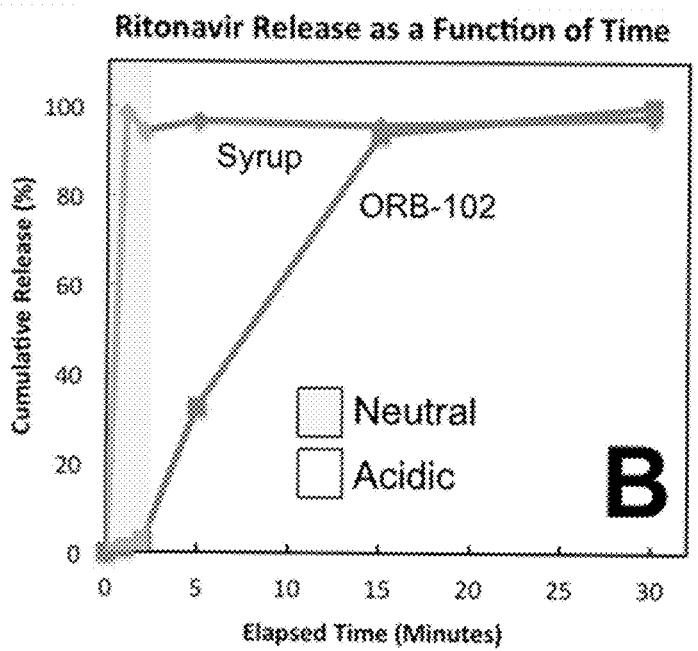

The results indicated that in neutral environments (similar to the oral cavity), the Orbis formulations were capable of mitigating API release during the first 2 minutes, and providing slow release afterwards. In acidic conditions (similar to the stomach and gastrointestinal tract), the formulations also mitigated API release during the first 2 minutes, but rapidly released drug thereafter. These kinetic properties, when considered in conjunction with one another (FIG. 3), demonstrate that the ORB-101 and ORB-202 formulations have the ability to mitigate drug release for the first 2 minutes in an oral environment, but then release drug in an accelerated fashion once reaching the lower pH environment of the stomach and GI tract. Specifically, at 2 minutes in a neutral environment, the ORB-101 and ORB-102 formulations had released 55 and 92% less API than the prednisone and ritonavir liquids, respectively. Importantly, both syrup formulations of prednisone and ritonavir reached full dissolution by 30 minutes, with over 90% cumulative release by 5 minutes.

ORB-101 and ORB-102 Formulations are Shelf-Stable for at Least One Month without Additional Drug Stabilization.

Figure 4:
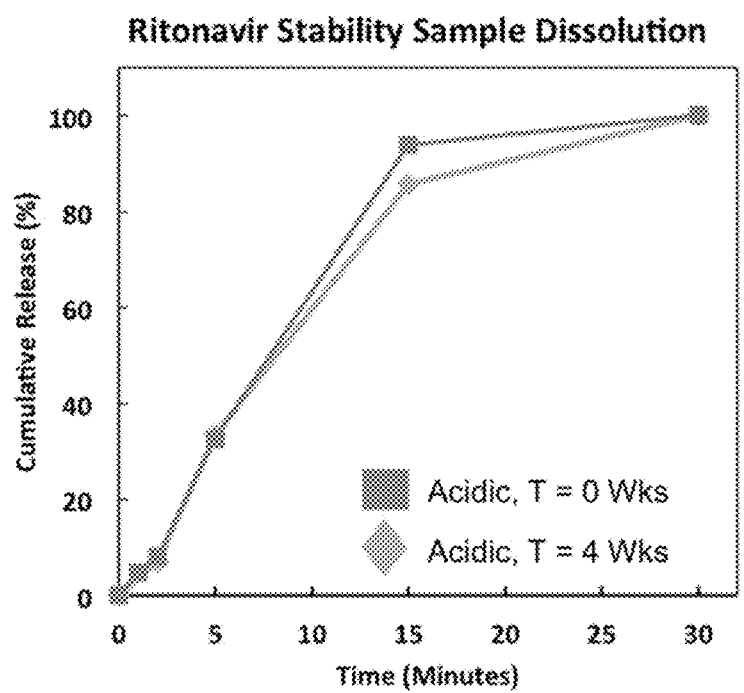
FIG. 4 provides dissolution profiles of ritonavir microcapusles in acidic conditions immediately after fabrication, and after storage for 4 weeks at 25° C.

Samples of core-shell prednisone and ritonavir capsules were retained in sealed glass vials at 25° C. for one month and then re-tested their dissolution behavior. Not only did the capsules have nearly identical release kinetics in neutral conditions compared to freshly-fabricated samples, they also displayed the previously-seen accelerated release in the acidic medium (FIG. 4). Moreover, the formulations displayed inherent shelf stability without any concerted stabilization efforts.

Figure 5:
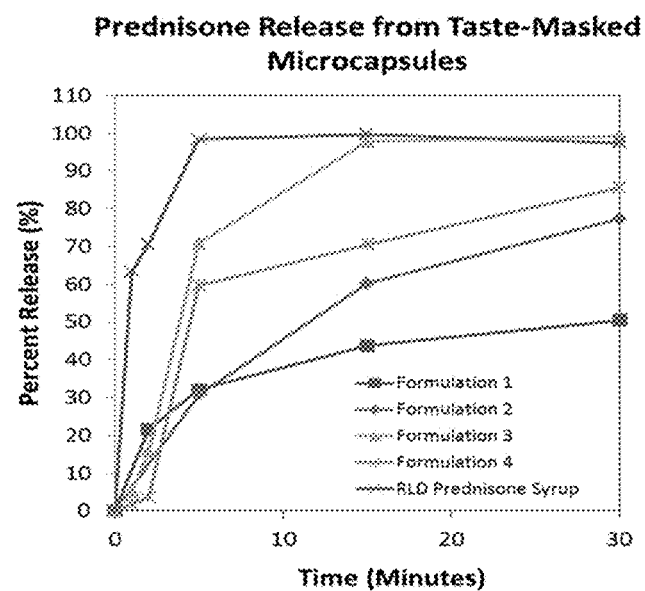
FIG. 5 provides dissolution profiles of prednisone (top) and ritonavir (bottom) microcapsules of the present disclosure in neutral (first 2 minutes) and acidic conditions thereafter (except for Formulations 1, 2, 5, and 6 which were maintained under neutral conditions for the duration) compared to their respective RLD syrup formulations.
Figure 5:
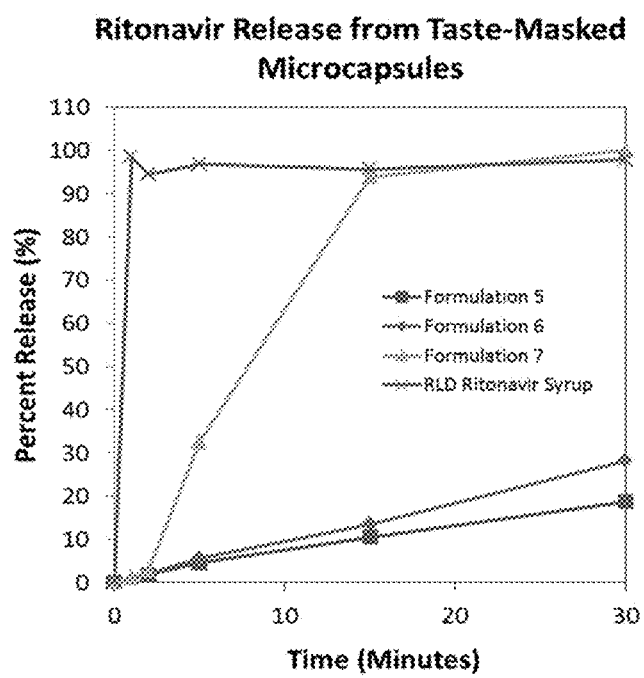

Dissolution Profiles of Various Microcapsule Formulations of Prednisone and Ritonavir The formulations in Table 1 were produced using PPF as described above. The dissolution studies for Formulations 1, 2, 5, and 6 were performed in 900 mL of a pH 2 solution using a USP Type II apparatus at 37° C. and 75 rpm. The dissolution studies for Formulations 3, 4, and 7 were performed in both 900 mL of a pH 7.4 and 900 mL of a pH 2 solution using a USP Type II apparatus at 37° C. and 75 rpm. The dissolution was performed in neutral conditions (pH 7.4) for the first 2 minutes, followed by the acidic conditions (pH 2) for 5-30 minutes. The dissolution profiles for Formulations 1-4 and 5-7 were compared to Prednisone syrup and Ritonavir syrup, respectively. The dissolution results are shown in FIG. 5.

TABLE 1

Prednisone and Ritonavir Formulations

| Formulation | Core (% w/w) | Shell (% w/w) |
|---|---|---|
| 1 | Prednisone - 3.0<br>PEG 2000 | Carnauba Wax - 100 |
| 2 | Prednisone - 2.7<br>PEG 2000 | Carnauba Wax - 64<br>Beeswax - 16<br>Stearic Acid - 10<br>Eudragit ® E PO - 10 |
| 3 | Prednisone - 2.7<br>PEG 2000 | Stearic Acid - 80<br>Eudragit ® E PO - 20 |
| 4 | Prednisone - 1.0<br>PEG 6000 | Stearic Acid - 80<br>Eudragit ® E PO - 20 |
| 5 | Ritonavir - 10.8<br>PEG 2000 | Carnauba Wax - 100 |
| 6 | Ritonavir - 19.3<br>PEG 2000 | Carnauba Wax - 80<br>Beeswax - 10<br>Eudragit ® E PO - 10 |
| 7 | Ritonavir - 6.7<br>PEG 2000 | Stearic Acid - 80<br>Eudragit ® E PO - 20 |

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A method for producing a microcapsule comprising the following steps:
   (1) dissolving an active pharmaceutical ingredient in ethanol to produce an active pharmaceutical ingredient-ethanol mixture;
   (2) co-melting the active pharmaceutical ingredient-ethanol mixture with a hydrophilic excipient to provide a core dispersion;
   (3) melting a pH-responsive material and a hydrophobic material comprising a wax or lipid to form a shell mixture which comprises about 1% to 25% by weight of the pH-responsive material in a hydrophobic matrix; and
   (4) applying the core dispersion through a central portion of a nozzle and simultaneously applying the shell mixture through an annular portion of the nozzle surrounding the central portion in the presence of vibrational excitation thereby forming the microcapsule, wherein the microcapsule comprises a core portion and a shell portion.

2. The method of claim 1 further comprising the step of applying a stabilizing air stream to the nozzle as the microcapsule exits the nozzle to reduce the diameter of the microcapsule.

3. The method of claim 1, wherein the hydrophilic excipient is one or more selected from the group consisting of polyethylene glycol, polyols, and poloxamer and lutrol block copolymers.

4. The method of claim 1 wherein the active pharmaceutical ingredient is hydrophobic.

5. The method of claim 1 wherein the pH-responsive material comprises a methacrylate copolymer, butylated methacrylate copolymer, basic butylated methacrylate copolymer, poly(methacrylic acid), amino methacrylate copolymer, aminoalkyl methacrylate copolymer, hydroxypropylmethyl cellulose phthalate, hypomellose phthalate, polyacrylate derivative or polymethacrylate derivative, and the hydrophobic matrix comprises a wax, lipid or combination thereof.

6. The method of claim 1 wherein the hydrophobic material is carnauba wax, beeswax, or a combination thereof.

7. The method of claim 1 wherein the hydrophobic material further comprises stearic acid.

8. The method of claim 1 wherein the pH-responsive material comprises a butylated methacrylate copolymer and the hydrophobic material comprises stearic acid.

9. The method of claim 1 wherein the active pharmaceutical ingredient is prednisone or ritonavir.

10. The method of claim 1 wherein the microcapsule has a mean particle diameter from about 100 µm to about 400 µm.

11. The method of claim 1, further comprising the step of suspending a plurality of the microcapsules in a liquid suspension.

12. The method of claim 1, further comprising the step of formulating a plurality of the microcapsules as a dry powder.

13. The method of claim 1 wherein the shell portion comprises from about 1% to 10% by weight of the pH-responsive material.

14. The method of claim 1 wherein the hydrophobic matrix further comprises a glycerol fatty acid ester, a cellulose ether, or a cellulose ester.

15. The method of claim 14 wherein the glycerol fatty acid ester is glycerol monostearate or a sorbitan ester.

* * * * *